(12) United States Patent
D'Acchioli et al.

(10) Patent No.: US 6,716,204 B1
(45) Date of Patent: Apr. 6, 2004

(54) ABSORBENT ARTICLE WITH IMPROVED FECES CONTAINMENT CHARACTERISTICS

(75) Inventors: Vincenzo D'Acchioli, Kelkheim (DE); Gianfranco Palumbo, Bad Homburg (DE); Donald C. Roe, West Chester, OH (US); Eva Susanne Dominique Thurnay, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/181,258

(22) Filed: Oct. 28, 1998

(51) Int. Cl.[7] ............................ A61F 13/15; A61F 13/20
(52) U.S. Cl. ............ 604/385.19; 604/369; 604/385.03; 604/387
(58) Field of Search .................... 604/327, 348, 604/355, 385.03, 385.12, 385.19, 386, 387, 401, 344, 345, 352

(56) References Cited

U.S. PATENT DOCUMENTS

| | | | |
|---|---|---|---|
| 1,059,992 A | 4/1913 | Heinrich | |
| 2,538,758 A | 1/1951 | Bricmont | |
| 3,292,626 A | 12/1966 | Schneider | |
| 3,340,876 A | 9/1967 | Hill | |
| 3,368,561 A | 2/1968 | Ericson et al. | |
| 3,522,807 A | 8/1970 | Millenbach | |
| 3,532,093 A | * 10/1970 | Lovret | 604/348 |
| 3,577,989 A | * 5/1971 | Anderson | 604/348 |
| 3,804,093 A | 4/1974 | Fell | |
| 3,890,973 A | * 6/1975 | Davis et al. | 604/355 |
| 3,906,952 A | 9/1975 | Zamist | |
| 4,072,151 A | 2/1978 | Levine | |
| 4,233,978 A | 11/1980 | Hickey | |
| 4,368,733 A | * 1/1983 | Sanidas | 604/327 |
| 4,484,919 A | 11/1984 | Sohn et al. | |
| 4,501,586 A | 2/1985 | Holtman | |

(List continued on next page.)

FOREIGN PATENT DOCUMENTS

| | | |
|---|---|---|
| EP | 0 585 904 | 3/1994 |
| EP | 0607986 A1 * | 7/1994 |

(List continued on next page.)

*Primary Examiner*—Karin Reichle
(74) *Attorney, Agent, or Firm*—David M. Weirich; Eileen L. Hughett; Edward J. Milbrada

(57) ABSTRACT

An absorbent article which includes a topsheet including a primary aperture for receiving fecal waste, a backsheet joined with at least a portion of the topsheet, an absorbent core disposed between at least a portion of the topsheet and the backsheet, and a spacing member disposed between the topsheet and the backsheet. The spacing member provides a void space into which feces can be directed. The absorbent article preferably also includes a body adhering composition disposed about at least a portion of the primary aperture for adhering the topsheet of the absorbent article to the wearer during use.

14 Claims, 4 Drawing Sheets

U.S. PATENT DOCUMENTS

| | | | |
|---|---|---|---|
| 4,596,244 A | 6/1986 | Jackson | |
| 4,662,877 A | 5/1987 | Williams | |
| 4,676,785 A | 6/1987 | Battista | 604/369 |
| 4,678,464 A | 7/1987 | Holtman | |
| 4,731,065 A * | 3/1988 | Yamada | 604/385 |
| 4,753,648 A | 6/1988 | Jackson | 604/389 |
| 4,784,656 A | 11/1988 | Christian | 604/355 |
| 4,892,536 A | 1/1990 | DesMarais et al. | |
| 4,968,312 A | 11/1990 | Khan | |
| 4,982,450 A | 1/1991 | D'Huissier | 2/402 |
| 4,990,147 A | 2/1991 | Freeland | |
| 5,037,416 A | 8/1991 | Allen et al. | |
| 5,062,840 A | 11/1991 | Holt et al. | |
| 5,114,419 A | 5/1992 | Daniel et al. | |
| 5,171,236 A | 12/1992 | Dreier et al. | 604/369 |
| 5,176,666 A | 1/1993 | Conway et al. | 604/349 |
| 5,176,672 A | 1/1993 | Bruemmer et al. | |
| 5,269,775 A | 12/1993 | Freeland et al. | |
| 5,304,159 A | 4/1994 | Tanji et al. | |
| 5,304,160 A | 4/1994 | Igaue et al. | |
| 5,306,266 A | 4/1994 | Freeland | |
| 5,330,459 A | 7/1994 | Lavon et al. | |
| 5,342,342 A | 8/1994 | Kitaoka | |
| 5,344,516 A | 9/1994 | Tanji et al. | 156/164 |
| 5,347,657 A | 9/1994 | Unsell | 2/67 |
| 5,397,319 A | 3/1995 | Suzuki et al. | |
| 5,417,680 A | 5/1995 | Kimura et al. | |
| 5,421,827 A | 6/1995 | Temple | 604/355 |
| 5,425,726 A | 6/1995 | Shimizu et al. | |
| 5,429,632 A | 7/1995 | Tanji et al. | |
| 5,439,459 A | 8/1995 | Tanji et al. | |
| 5,445,627 A | 8/1995 | Mizutani et al. | |
| 5,462,541 A | 10/1995 | Bruemmer et al. | 604/391 |
| 5,520,674 A | 5/1996 | Lavon et al. | |
| H1602 H | 10/1996 | Brock | 604/387 |
| 5,582,604 A | 12/1996 | Ahr et al. | |
| 5,586,978 A | 12/1996 | Bayne | 604/327 |
| 5,593,397 A | 1/1997 | La Gro | 604/355 |
| 5,651,778 A | 7/1997 | Melius et al. | |
| 5,653,842 A | 8/1997 | Kuen | 156/227 |
| 5,658,270 A | 8/1997 | Lichstein | 604/387 |
| 5,702,381 A | 12/1997 | Cottenden | |
| 5,779,690 A | 7/1998 | Gustafsson et al. | |
| 5,807,367 A | 9/1998 | Dilnik et al. | 604/369 |
| 5,830,203 A * | 11/1998 | Suzuki et al. | 604/385.19 |
| 5,853,403 A * | 12/1998 | Tanzer et al. | 604/385.19 |
| 5,876,393 A * | 3/1999 | Ahr et al. | 604/385.12 |
| 5,997,520 A * | 12/1999 | Ahr et al. | 604/385.12 |
| 6,132,409 A * | 10/2000 | Vogt et al. | 604/348 |
| 6,156,818 A * | 12/2000 | Corzani et al. | 523/111 |
| 6,168,584 B1 * | 1/2001 | Allen et al. | 604/385.19 |
| 6,565,549 B1 * | 5/2003 | Allen et al. | 604/385.04 |
| 6,572,600 B1 * | 6/2003 | Roe et al. | 604/389 |
| 6,595,972 B1 * | 7/2003 | Wise et al. | 604/385.01 |
| 6,623,465 B1 * | 9/2003 | Roe et al. | 604/385.03 |

FOREIGN PATENT DOCUMENTS

| | | |
|---|---|---|
| EP | 0 626 161 | 11/1994 |
| EP | 0 758 543 | 2/1997 |
| EP | 0 850 628 | 7/1998 |
| EP | 0 887 063 A1 | 12/1998 |
| GB | 2268073 | 1/1994 |
| JP | 3049296 | 3/1998 |
| JP | 3048845 | 5/1998 |
| WO | 91/09582 | 7/1991 |
| WO | 93/25172 | 12/1993 |
| WO | 95/16417 | 6/1995 |
| WO | 95/16418 | 6/1995 |
| WO | 95/16422 | 6/1995 |
| WO | 95/16424 | 6/1995 |
| WO | 95/25493 | 9/1995 |
| WO | 95/25494 | 9/1995 |
| WO | 96/09026 | 3/1996 |
| WO | 96/23466 | 8/1996 |
| WO | 96/23467 | 8/1996 |
| WO | 97/01316 | 1/1997 |
| WO | 97/14385 | 4/1997 |
| WO | 97/17926 | 5/1997 |
| WO | 97/24093 | 7/1997 |
| WO | 97/49366 | 12/1997 |
| WO | 98/17219 | 4/1998 |
| WO | 98/23305 | 6/1998 |
| WO | 98/27909 | 7/1998 |
| WO | 98/27910 | 7/1998 |
| WO | 98/27911 | 7/1998 |
| WO | 98/27912 | 7/1998 |
| WO | 98/27913 | 7/1998 |
| WO | 98/27915 | 7/1998 |
| WO | 98/27916 | 7/1998 |
| WO | 98/27918 | 7/1998 |
| WO | 98/28017 | 7/1998 |
| WO | 98/37838 | 9/1998 |
| WO | 98/37839 | 9/1998 |
| WO | 98/47457 | 10/1998 |
| WO | WO 00 24350 A1 * | 5/2000 |

* cited by examiner

ABSORBENT ARTICLE WITH IMPROVED FECES CONTAINMENT CHARACTERISTICS

FIELD OF THE INVENTION

This invention is directed to hygienic absorbent articles, such as diapers, adult incontinence articles, feminine protection articles and the like.

BACKGROUND OF THE INVENTION

Absorbent articles are well known in the art. These articles typically have an absorbent core, which is held or positioned against the body of the wearer during use by a fastening system, such that the bodily exudates are caught by the article. Typical absorbent articles include a topsheet facing the wearer which permits fluid exudates to pass through and a backsheet which prevents the exudates from escaping from the absorbent article.

Many advancements have been made in the art since the introduction of the disposable absorbent article. However, problems still exist relating to the acceptance and storage of feces, and especially runny and pasty feces. The problem has been difficult to resolve because feces generally will not pass through a topsheet and thus, remains free to move about in the diaper until the diaper is changed. This often leads to feces escaping the diaper or soiling of the wearer's skin.

In order to prevent the feces from escaping the diaper or soiling the skin, apertures have been provided in the topsheet which allow the feces to pass to the absorbent core. However, the apertures are difficult to position during application of the diaper and often move from the desired position when the diaper is worn.

Thus, it would be desirable to provide absorbent articles with improved fit and sealing which can be sustained during use. It would also be desirable to provide an article which can maintain a desired configuration for accepting and storing body exudates, especially feces. Further, it would be advantageous to provide an article with a topical or body adhesive which helps maintain the article in the desired configuration (e.g., the aperture is aligned with the anus) without irritating or harming the wearer's skin. Even further, it would also be advantageous to provide a void space for the waste which can be maintained even under applied pressures which are typical of the forces generated by a wearer on the crotch and buttocks region of the article while the wearer is in a seated position.

SUMMARY OF THE INVENTION

In order to solve one or more of the problems found in the art, an absorbent article, such as an adult incontinence article, baby diaper or feminine hygiene pad, having a void space created by a spacing member capable of withstanding at least 0.5 psi while compressing no more than 60% is provided. The article also has a topical adhesive which helps keep the article in a desired configuration for receiving and storing bodily exudates. Preferably, the absorbent article comprises a topsheet including a primary aperture for receiving fecal waste, a backsheet joined with at least a portion of the topsheet, an absorbent core disposed between at least a portion of the topsheet and the backsheet, and the spacing member disposed between the topsheet and the backsheet. The spacing member provides a void space into which feces can be directed. The absorbent article preferably also includes a body adhering composition disposed about at least a portion of the primary aperture for adhering the topsheet of the absorbent article to the wearer during use.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element. A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, wipes, mops, bandages and the like.

Figure 1:
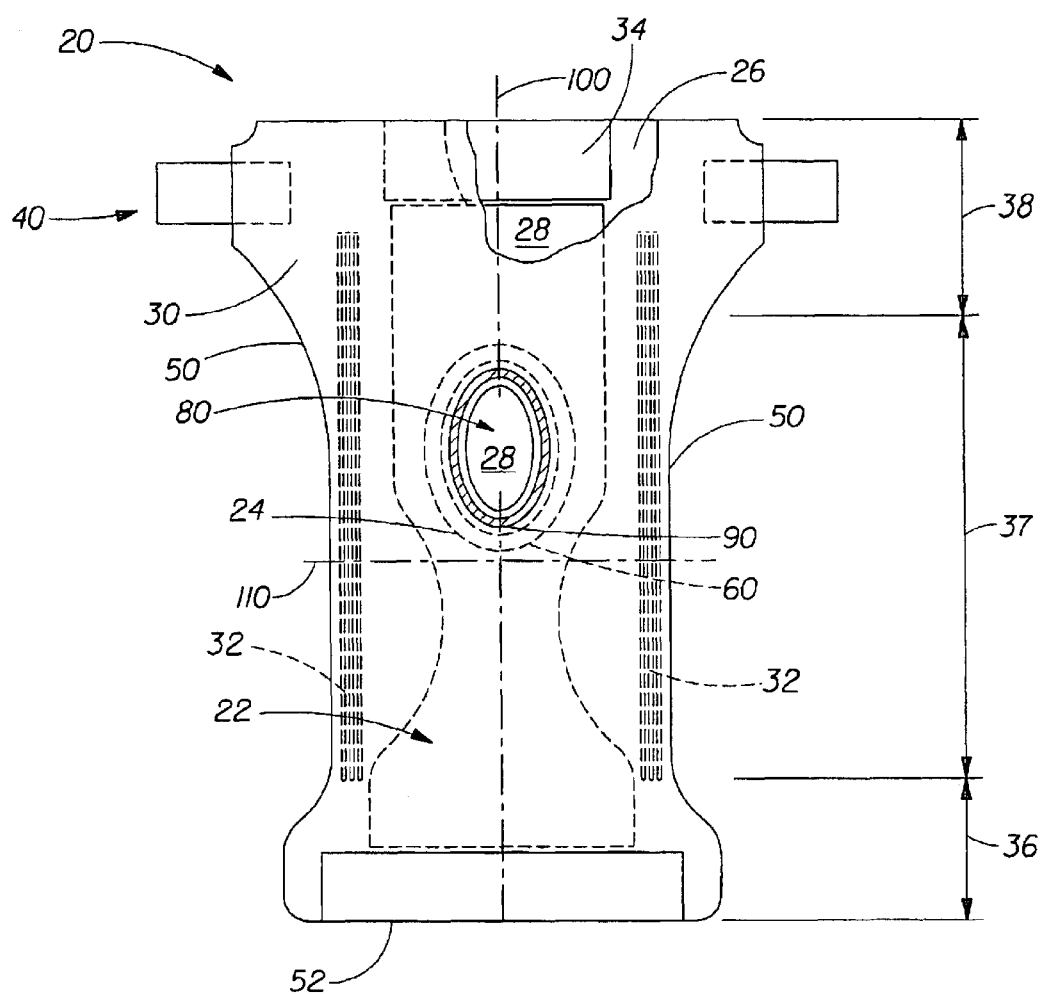
FIG. 1 is a plan and cutaway view of a disposable diaper.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 is shown in FIG. 1 to have a first waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The backsheet 26 is generally that portion of the diaper 20 positioned adjacent the garment facing surface of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996, now U.S. Pat. No. 5,865,823 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. Preferably, one of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body facing surface of the absorbent core 28 and may be partially or wholly joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet may comprise one or more apertures 80 to ease penetration of exudates therethrough, such as urine and/or feces (solid, semi-solid, or liquid). The size of at least the primary aperture 80 is important in achieving the desired waste encapsulation performance. If the primary aperture 80 is too small, the waste may not pass through the aperture, either due to poor alignment of the waste source and the aperture location or due to fecal masses having a diameter greater than the aperture 80. If the aperture 80 is too large, the area of skin that may be contaminated by "rewet" from the article is increased. Typically, the aperture 80 should have an area of between about 10 cm$^2$ and about 50 cm$^2$. The aperture 80 preferably has an area of between about 15 cm$^2$ and 35 cm$^2$.

Further, the topsheet may be fully or partially elasticated or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which are incorporated by reference herein.

The topsheet 24 is preferably compliant, soft feeling, and non-irritating to the wearer's skin. Further, at least a portion of the topsheet 24 is liquid pervious, permitting liquids to readily penetrate through its thickness. At least a portion of the topsheet 24 may be impermeable to liquids and solids or semi-solids or may be permeable to exudates only in a direction away from the wearer. Further, the topsheet 24 may include regions of differing permeability. For example, the topsheet 24 may be liquid permeable in the urine loading region of the diaper (generally front waist region and/or crotch region) and may be impermeable in the area surrounding the aperture 80. This provides good urine acquisition characteristics while preventing feces which pass through the aperture 80 from passing back towards the wearer's skin. The remainder of the topsheet may additionally comprise a multiplicity of secondary apertures as described in more detail in U.S. Pat. No. 5,342,338 issued to Roe on Aug. 30, 1994 entitled "Disposable Absorbent Article For Low-Viscosity Fecal Material". These secondary apertures generally have an area which is less than the area of the primary aperture but provide a means for low viscosity bodily wastes to penetrate the topsheet 24 if the wastes contact the topsheet 24 in a region other than that of the primary aperture 80.

A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheet includes fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Massachusetts under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets are made in accordance with U.S. Pat. Nos. 4,609,518 and 4,629,643, which issued to Curro et al. on Sep. 2, 1986 and Dec. 16, 1986, respectively, and both of which are incorporated herein by reference. Such formed films are available from The Procter & Gamble Company of Cincinnati, Ohio as DRI-WEAVE and from Tredegar Corporation of Terre Haute, Ind. as CLIFF-T.

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple/Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein. Alternatively, the topsheet 24 may include an apertured web or film which is hydrophobic. This may be accomplished eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

Exemplary absorbent structures for use as the absorbent core are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,650,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The diaper 20 may also include a sublayer disposed between the topsheet 24 and the backsheet 26. The sublayer may be any material or structure capable of accepting, storing or immobilizing bodily exudates. Thus, the sublayer may include a single material or a number of materials operatively associated with each other. Further, the sublayer may be integral with another element of the diaper 20 or may be one or more separate elements joined directly or indirectly with one or more elements of the diaper 20. Further, the sublayer may include a structure that is separate from the core 28 or may include or be part of at least a portion of the core 28.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and more specifically, having pores greater than about 1.0 mm in diameter.) One embodiment of a storage element includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent storage elements are described in European Patent Application No. EP 0 847 738 A1 entitled "Disposable Absorbent Article Having Capacity to Store Low-Viscosity Fecal Material" published Jun. 17, 1998 in the name of Roe, which is hereby incorporated by reference herein. Further, the sublayer, or any portion thereof, may include or be coated with a lotion or other known substances to add, enhance or change the performance or other characteristics of the element.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. The fastening system 40 preferably maintains the first waist region 36 and the second waist region 38 in an overlapping configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151, 092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963, 140 issued to Robertson et al. on Oct. 16, 1990. Each of these patents is incorporated herein by reference. In alternative embodiments, opposing sides of the garment may be seamed or welded to form a pant. This allows the article to be used as a pull-on type diaper, such as a training pant.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application, the diaper 20 will "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151, 092 issued to Buell on Sep. 9, 1992; and U.S. Pat. No. 5, 221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.; each of which is incorporated herein by reference.

The diaper 20 preferably further includes leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,062,840, entitled "Disposable Diapers", issued to Holt et al. on Nov. 5, 1991; and U.S. Pat. No. 5,269,775 entitled "Trisection Topsheets For Disposable Absorbent Articles And Disposable Absorbent Articles Having Such Trisection Topsheets", issued to Freeland et al. on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Pat. No. WO 94/14395 entitled "Absorbent Article Having An Upstanding Transverse Partition" published Jul. 7, 1994 in the name of Freeland et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

Preferred embodiments of the present invention are particularly suited to the entrapment or encapsulation of bodily waste and thus reduce the amount and area of contamination of the wearer's skin by the waste. In order to achieve the desired level of performance, especially for viscous bodily waste such as feces, at least two functions should be performed. First, the diaper should have means of maintaining proximity of the accepting element of the diaper (e.g., an aperture in the topsheet) to the wearer's waste exit point (e.g., anus) of the wearer. Second, the diaper should provide a void space 70 for the waste even under applied pressures which are typical of those generated by a wearer on the crotch and buttocks regions of the article while the wearer is in a seated position.

In order to provide a void space 70 which can be maintained under pressure, preferred embodiments of the present invention include one or more spacers or spacing members 60. The spacing member(s) 60 are intended to space the topsheet 24 or other covering layer away from the absorbent core 28 and/or other underlying layers such as sublayers, acquisition layers and the like. However, it is also contemplated that the spacing member 60 may space apart any other two elements of the diaper 20, including but not limited to the topsheet 24 and the backsheet 26, the acquisition layer and the core 28, the core 28 and the backsheet 26, etc. Nonlimiting, exemplary spacers 60 are disclosed in the patents incorporated by reference above.

Figure 3:
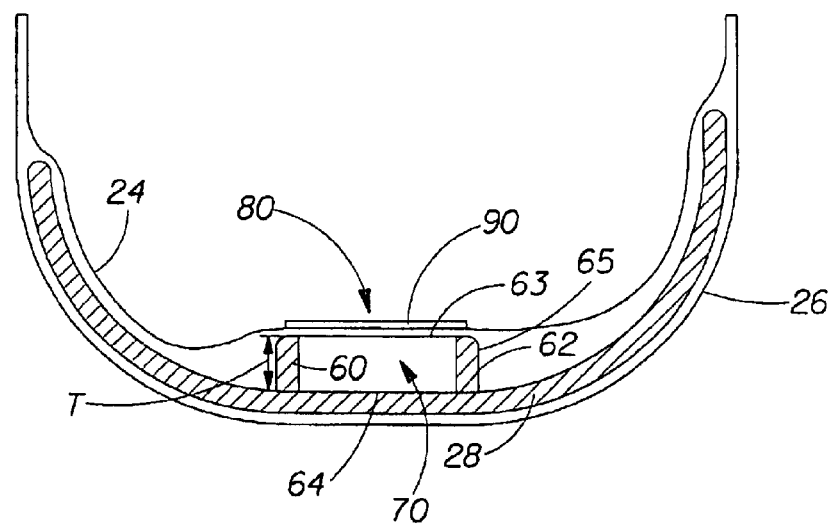
FIG. 3 is a cross-sectional view of one embodiment of the present invention shown as it may appear when worn.
Figure 4:
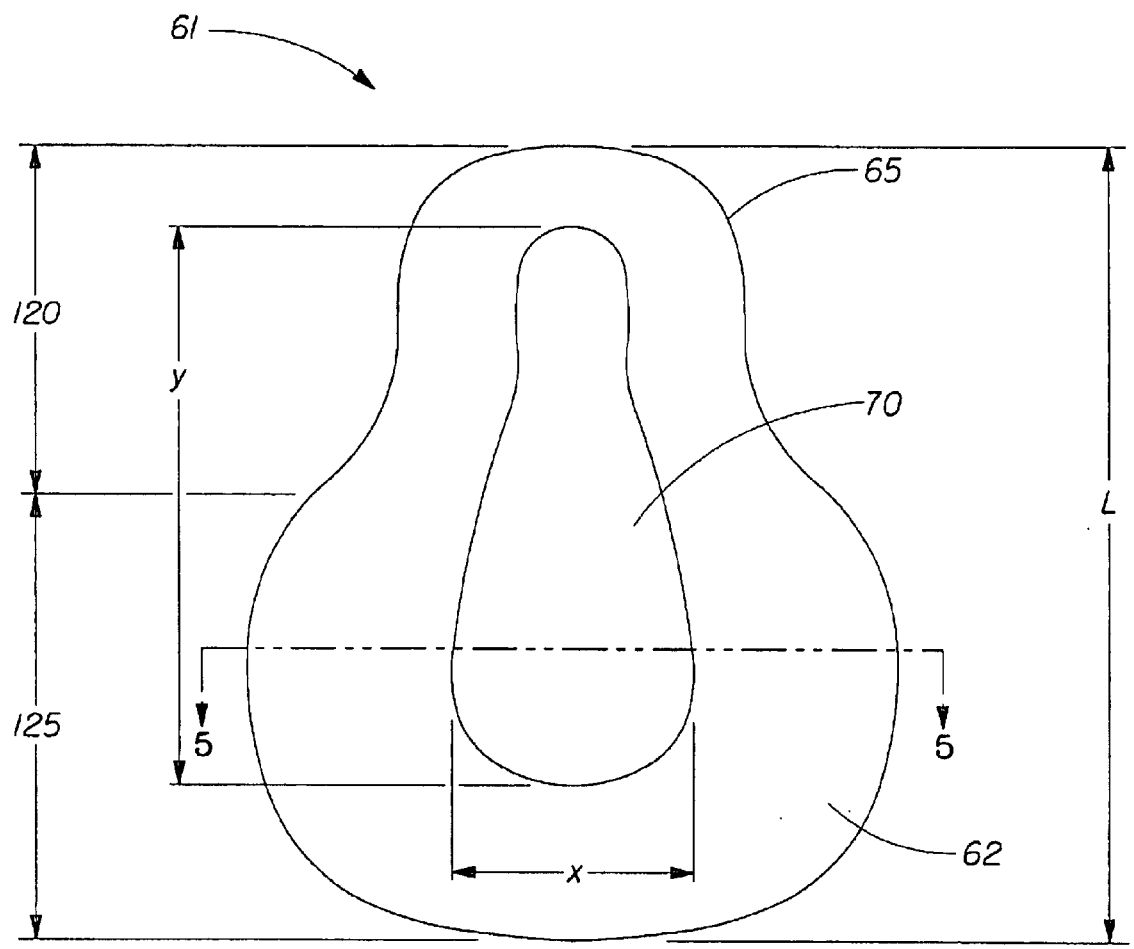
FIG. 4 is a plan view of a spacing member suitable for use with the present invention.
Figure 5:
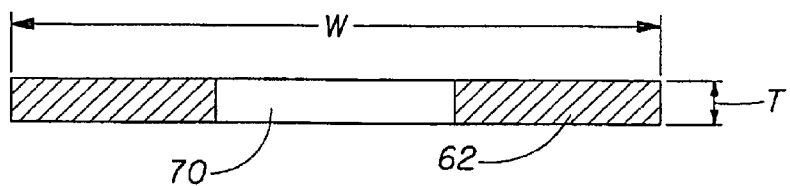
FIG. 5 is a cross-sectional view of the spacing member shown in FIG. 4 taken through section line 5—5.

The spacing member 60 may be of any suitable size and/or shape. In preferred embodiments, please refer to FIG. 3, the spacing member 60 has a body facing side 63, a backsheet facing side 64 and a thickness T of between about 0.5 cm and about 3.0 cm in use. (As used herein, the thickness T of the spacer 60 is the distance between the body facing side 63 and the garment facing side 64 of the spacer 60.) Further, it is preferred that the spacer 60 create and maintain during use a void space 70 of between at least about 10 cubic cm and about 150 cubic cm, and preferably between about 25 cubic cm and about 75 cubic cm. It is also important that the lateral dimension X, as shown in FIG. 4, of the void space 70 be large enough to accommodate the feces, but narrow enough such that the spacing member 60 can support the ischia of the wearer. Preferably, the lateral dimension X of the void space 70, defined by the spacer 60 in the area corresponding to the anus of the wearer, is between about 1 cm and about 5 cm, and more preferably between about 1.5 cm and about 3.5 cm.

Although the shape of the spacer is not critical, it has been found that elliptical and "keyhole" shaped spacers (e.g. the spacer 61 shown in FIG. 4) perform particularly well. If such a spacer is implemented, it is preferred that the spacer 61 be disposed generally in the crotch region 37 of the diaper 20 and oriented such that the first region 120 of the spacer 61 is located toward the front waist of the diaper 20 when worn and the second region 125 of the spacer is located toward the rear waist of the diaper 20 when worn. Alternatively, U-shaped spacers may be suitable for use in certain embodiments (preferably with the open end of the U-shape oriented toward the rear waist region of the diaper 20 when worn). In any case, the spacer may be unitary or may comprise a multiplicity of separate or operatively associated parts. Further, the spacer 60 may have a closed perimeter or may comprise openings, holes, or channels extending from the fecal void space 70 through the spacer wall 62 to the perimeter of the spacer 60. Such embodiments may be useful to allow distribution of feces from the void space 70 to other parts of the diaper 20.

The spacing member 60 may comprise any material or combination of materials which are suitable for use in an absorbent article to be worn by a human wearer. For example, the spacing member 60 may include foams, woven or nonwoven webs, thermoplastic materials, organic materials, fibers, gels, rubber or synthetic rubber, etc. In one preferred embodiment, the spacing member 60 comprises an absorbent foam made from a 16:1 water/oil emulsion, having a glass transition temperature of about 10° C., and having a compression of about 40% in a dry state and about 30% in a wet state (i.e., when saturated with water) under about 1.0 psi applied pressure. Thus, in certain embodiments, the compression under about 1.0 psi in the wet state may be less than the compression under about 1 psi in the dry state.

In a preferred embodiment, the spacing member 60 is relatively soft, but resilient and capable of withstanding the forces typical of a baby's movements and/or the weight of a baby sitting or lying on the spacing member 60. Thus, the spacing member 60 should be capable of withstanding at least 0.5 psi and preferably at least about 1.0 psi while compressing no more than about 60%, and preferably no more than about 30% in both wet and dry conditions.

In yet another embodiment, the spacing member 60 may be activatable during use. That is, the spacing member 60 may be stored in the diaper 20 in one configuration and may be activated by some event or material which changes the configuration of the spacing member 60 or the surrounding structure so as to provide the diaper 20 with a desired configuration for receiving and/or storing bodily exudates. For example, the spacing member 60 may include a material which expands when contracted by water, urine, feces, enzymes or other means associated with the wearer's body or bodily exudates. Changes in temperature, pH and saline concentration are also "triggers" which can activate the spacing member 60. Thus, when the wearer urinates, the spacing member 60 may increase in thickness, change shape or otherwise orient itself in the diaper 20 to provide a void space 70 into which urine and/or feces can flow.

In preferred embodiments, at least a portion of the spacing member 60 is joined to the topsheet 24. This helps keep the primary aperture 80 aligned with the void space 70 of the spacer 60 during use. It is also preferred that at least a portion of the spacer 60 be joined with at least a portion of the structure which underlies the spacer 60, such as the core 28, a sublayer or the backsheet 28. In any case, the spacer 60 may be joined directly or indirectly by any means known in the art. Typical joining means include adhesives, heat, pressure, static, magnetism, snaps, hook and loop fasteners and the like.

Figure 2:
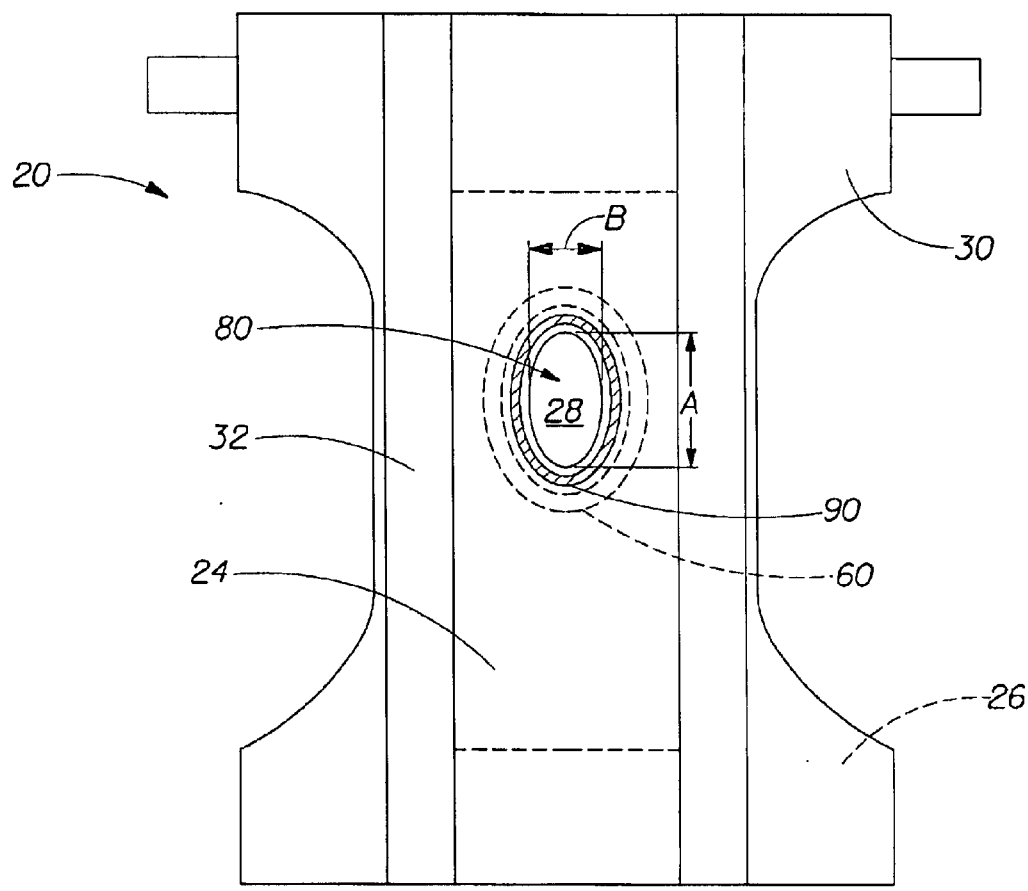
FIG. 2 is a plan view of a disposable diaper configuration of the present invention.

The advantages of a diaper including an apertured topsheet and a spacing member 60 are significantly reduced if the aperture 80 does not stay aligned with the wearer's anus and the void space 70 provided by the spacer 60 throughout the time of use (or at least until the wearer has a bowel movement). Accordingly, the diaper 20 of the present invention is preferably provided with a means for maintaining the aperture 80 in alignment with the wearer's anus. Preferably, the diaper 20 includes a topical adhesive or body adhering composition which acts to hold the aperture 80 in place during use. As shown in FIG. 2, the topical adhesive 90 may be located on the topsheet 24. However, the body adhering composition 90 may also be integral with the material making up the topsheet 24 or other element of the absorbent article or may be a separate material disposed directly or indirectly on all or any portion of the absorbent article. Further, the body adhering composition 90 may be disposed on any portion of the absorbent article in any pattern or configuration including, but not limited to lines, stripes, dots, and the like.

In one preferred embodiment, the topical adhesive 90 is disposed on the topsheet 24 in a continuous ring about the aperture 80. However, embodiments are contemplated wherein the topical adhesive 90 surrounds only a portion of the aperture 80 and/or is disposed in locations not directly adjacent the aperture 80, such as around the edge of the topsheet 24, on the leg cuffs 32 or in one or both of the waist regions. Alternatively, topical adhesive 90 may be disposed on the spacer 60 itself. If this is done, the topical adhesive 90 may be on an exposed surface of the spacer 60 or may be located beneath an apertured, slit or otherwise reticulated layer such that the topical adhesive 90 can contact the wearer in use.

The body adhering composition 90 may include any one or more substances capable of releasably adhering to the skin of the wearer. Further, the body adhering composition 90 may be in the form of a gel, lotion, film, web or the like. Examples of suitable body adhering compositions include adhesives, gelatin, petrolatum, waxes such as silicone or petroleum waxes, oils such as silicone or petroleum based oils, skin care compositions or ingredients thereof, as described below, and the like. Suitable topical adhesives include, but are not limited to, hydrogel or hydrocolloid adhesives such as acrylic based polymeric adhesives, and the like. (Some exemplary hydrogel and/or hydrocolloid adhesives are disclosed in U.S. Pat. Nos 4,231,369; 4,593,053; 4,699,146; 4,738,257; and 5,726,250; each of which is incorporated by reference herein.) The topical adhesives may also include any "medical adhesive" which is compatible for use with biological tissue, such as skin. Acrylic medical adhesives suitable for use as body adhering compositions 90, include adhesives available from Adhesive Research, Inc., of Glen Rock, Pa., under the designations MA-46, MA-312, MTTM High MVTR adhesive, and AS-17. Rubber-based medical adhesives, such as SB-2 from Adhesive Research Inc. may also be suitable. Other exemplary adhesives include Dow Corning Medical Adhesive Type B) available from Dow Corning, Midland, Minn.; MEDICAL ADESIVE from Hollister Inc., of Libertyville, Ill.; 3M Spray Adhesives #79, 76, 77 and 90 available from the 3M Corp. of St. Paul, Minn.; and MATISOL liquid adhesive available from Ferndale Laboratories of Ferndale, Minn. Other medical adhesives are described in U.S. Pat. Nos. 4,078,568; 4,140,115; 4,192,785; 4,393,080; 4,505,976; 4,551,490; 4,768,503 and polyacrylate and polymethacrylate hydrogel adhesives are disclosed in U.S. Pat. Nos. 5,614,586 and 5,674,275; the disclosure of each of which is incorporated by reference herein. Yet another exemplary adhesive comprising polyvinyl pyrollidone and a multi-functional amine-containing polymer is disclosed in WO 94/13235A1. (The disclosure of each of these references is incorporated herein by reference.) Alternative body adhering means, which may be used in place of or in addition to those described above, include static electricity, suction and the like. In any case, it is preferred that the body adhering composition 90 permit vapors to pass (i.e., breathable), be compatible with the skin and otherwise skin friendly. Further, it is preferred that the body adhesive 90 be at least partially hydrophobic, preferably 60%, more preferably 80%, by weight of the adhesive consist of hydrophobic components. However, hydrophilic adhesives are contemplated in certain embodiments of the present invention.

In preferred embodiments as described in co-pending EPO Application nos. 96120738.8, 97110730.5 and 97120336.9 (each of which are incorporated by reference herein), removal of the body adhering composition from the skin is relatively painless. In these embodiments, the body adhesive or body adhering composition has an elastic modulus at a temperature of 37° C. (100° Fahrenheit) abbreviated $G'_{37}$ and a viscous modulus at a temperature of 37° C. (100° Fahrenheit) of $G''_{37}$. The adhesive further has a dynamic elastic behavior defined as $\Delta G'_{37}$ which is the difference of $G'_{37}$ at a frequency of 100 rad/sec and $G'_{37}$ at a frequency of 1 rad/sec and a dynamic viscous behavior $\Delta G''_{37}$ which is the difference of $G''_{37}$ at a frequency of 100 rad/sec and $G''_{37}$ at a frequency of 1 rad/sec. Further, the body adhesive preferably satisfies the following conditions.

$G'_{37}$ (1 rad/sec) is in the range of about 1500 Pa to about 20000 Pa, preferably of about 1500 Pa to about 15000 Pa, most preferably of about 3000 Pa to of about 10000 Pa.

$G''_{37}$ (1 rad/sec) is in the range of about 100 Pa to about 15000 Pa, preferably of about 100 Pa to of about 10000 Pa, most preferably 300 Pa to of about 5000 Pa.

The ratio of $G'_{37}$ (1 rad/sec)/$G''_{37}$ (1 rad/sec) is in the range of about 3 to about 30.

The ratio $G'_{37}$ (100 rad/sec)−$G''_{37}$ (100 rad/sec)/$G'_{37}$ (1 rad/sec)−$G''_{37}$ (1 rad/sec) is not less than about 0.5, preferably in the range of about 0.7 to 3, most preferably in the range of about 1 to about 1.8.

The ratio of $\Delta G'_{37}/G'_{37}$ (1 rad/sec) is not greater than about 1.5, preferably not greater than about 0.8, or $\Delta G'_{37}$ is not greater than about 10000 Pa, preferably less than 5000 Pa, most preferably less than about 2000 Pa, or both.

The value of the ratio $G'_{37}/G''_{37}$ at least for the frequency range from about 1 rad/s up to 100 rad/s should preferably be about 3.3 or above, more preferably about 5 or above, most preferably about 10 or above while not exceeding about 50, or preferably about 30 anywhere in the frequency interval.

To obtain the desired characteristics, the body adhering composition 90 may comprise: from 0.5 to 20%, preferably 5% to 15%, by weight of a macromolecular or polymeric substance or a mixture of such substances soluble or swellable in the below mentioned plasticizer(s). As not limiting examples such macromolecular or polymeric substances can be natural and/or synthetic such as natural gums or derivatives such as natural gums and gelatins, their derivatives and alginates; polyacrylics; polyvinyl alcohol; polyethylene oxide; polyvinylpyrrolidon (PVP) or polyvinylethers, their copolymers and derivatives; cellulose derivatives; Block Copolymer Thermoplastic Elastomers and preferably Styrenic block Copolymers and more preferably the hydrogenated grades Styrol/Ethylene-Butylene/Styrol (SEBS), Styrene/Isoprene/Styrene (SIS), and Styrol/Ethylene-Propylene/Styrol (SEPS). Further, preferred body adhesive compositions may comprise from 45 to 99.5% by weight, preferably from 51 to 99.5% by weight, of a plasticizing substance or a mixture of plasticizing substances, which are liquid at room temperature. As non-limiting examples the plasticizer can be water, various alcohols (like in particular glycerol), glycols and their ethers, polyglycols, liquid polybutenes, esters such phtalates, adipates, stearates, palmitates, sebacates, or myristates, natural or synthetic oils such as vegetable oils, mineral oils, or combinations thereof. Further, the body adhesive may include from 0% to 50% by weight of the composition, preferably 0% to 600% by weight of the macromolecular polymeric substance, of a tackifying resin whose main scope is to tailor the Tg especially in systems based on synthetic polymers. Also, preferred body adhesives may include from 0 to 10% and more preferably from 0 to 5% by weight of substances for facilitating and stabilizing the gel and the gel forming process both of hydrophilic or hydrophobic liquid plasticizers. These may be for oily systems, e.g., the fatty acids of $C_8$ to $C_{22}$, their metallic salts and their polyoxo-derivatives; lanolin derivatives; silica; bentonite, montmorillonite and their derivatives; polyamides, waxes or mixtures thereof.

Common additives known in the art as preservative, antioxidants, anti UV, pigments, mineral fillers, rheology modifiers and the like can also be comprised in quantities up to 10% each. Also, when chemical crosslinks are formed in the system, a cross-linking agent can be present preferably in quantities up to 5% by weight. Chemical crosslinking can be formed also by mutual neutralization of polymers having different functionalities as in the reaction between acid polyacrylics and polysaccharides.

Suitable skin care compositions which may be used as, with, or in place of the body adhering compositions include Category I actives as defined by the U.S. Federal Food and Drug Administration's (FDA) Tentative Final Monograph on Skin Protectant Drug Products for Over-the-Counter Human Use, which presently include: alantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Federal Food and Drug Administration's Tentative Final Monograph on Skin Protectant Drug Products for Over-the-Counter Human Use tentative final monograph on skin protectant drug products for over-the-counter human use, which presently include: live yeast cell derivatives, aldioxa, aluminum acetate, microporous cellulose, cholecalciferol, colloidal oatmeal, cysteine hydrochloride, dexpanthenol, Peruvian balsam oil, protein hydrolysates, racemethionine, sodium bicarbonate, Vitamin A, and the like. Many of the FDA monographed skin care ingredients are currently utilized in commercially available skin care products, such as A AND D Ointment, VASELINE Petroleum Jelly, DESITIN Diaper Rash Ointment and Daily Care Ointment, GOLD BOND Medicated Baby Powder, AQUAPHOR Healing Ointment, BABY MAGIC Baby Lotion, JOHNSON'S ULTRA SENSITIVE Baby Cream, Johnson's baby lotion, lip balms, etc. Other suitable skin care compositions (e.g., lotions) are described in detail in U.S. Pat. Nos. 643,588; 5,607,760; 5,600,587; and 5,635,191; each of these references being incorporated herein by reference.

The skin care compositions may also include feces chemical modification agents, pH control agents, enzyme inhibitors, antimicrobials, odor absorbing agents (such as cyclodextrins or activated charcoal), or antimicrobials. Examples of enzyme inhibitors include protease inhibitors (e.g., hexamidine derivatives), lipase inhibitors (e.g., triacetin), urease inhibitors, and the like. Citric acid is an example of a suitable proton-donating pH control agent. In one preferred embodiment, a skin care composition comprising about 57% by wt. petrolatum, about 42% by wt. stearyl alcohol, and about 1% aloe extract is applied to about the topsheet 24 about the aperture 80 at add-on level of at least about 5 mg/cm$^2$.

EXAMPLE

One preferred embodiment of the present invention is an absorbent article as is generally shown in FIG. 2. The absorbent article is provided with a nonwoven topsheet 24 (e.g., P-8 available from Veratec, Inc.) including an elliptical aperture 80 having an open area of about 17 cm$^2$. (As used herein the term "open area" refers to the plan view area of the aperture.) In a preferred embodiment, the aperture 80 has a longitudinal dimension A of about 6 cm and a lateral dimension B of about 3.5 cm. The aperture 80 is preferably located in approximately the area of the diaper 20 associated with the wearer's anus. A layer of PG-70 adhesive 90 (available on a one mm thick open cell foam substrate from First Water Co., of Coventry, England) is applied to the topsheet 24 in the area immediately surrounding the aperture 80 in about a 1 mm thick and about 1.5 cm wide band.

An absorbent foam spacer 60, 61 is disposed between the topsheet 24 and the backsheet 26 and is affixed to the underlying structure (e.g., core 28) of the diaper 20 such that the void space 70 created by the spacer 60 is aligned with the aperture 80 in the topsheet 24. The spacer can also have a "keyhole" geometry, see spacer 61 as shown in FIG. 4. Further, the spacer 61 has a thickness T of about 1.25 cm, a void space area of about 24 cm$^2$, a width W of about 3.5 cm in the region corresponding approximately to the anus, and a void space volume of about 33 cm$^3$. (As used herein the term "void space area" means the plan view area of the void space 70. Void space volume as used herein is the volume of the void space created by the spacer 61.) The void space 70 preferably has a length Y of about 8.4 cm and a width X of about 3.9 cm. The spacer 60 preferably compresses no more than about 60%, more preferably 30% under a 1.0 psi load when the spacer 61 is in a dry state, and no more than about 60%, more preferably 30% under a 1.0 psi load when wet or saturated (e.g., with water).

The spacer 60 preferably includes an absorbent foam made from a 16:1 water/oil emulsion, having a glass transition temperature of about 10° C., and having a compression of about 43% dry and about 32% wet under about 1.0 psi applied pressure. At least a portion of the spacer 60 is attached to the absorbent core 28. (The spacer 60 may be also or alternatively joined with another underlying element such as a sublayer, a secondary topsheet or the backsheet). It is also preferred that the spacer 60 be joined to the topsheet 24 along some or all of the spacer's perimeter 65. This helps keep the aperture 80 in the topsheet 24 aligned with the void space 70 of the spacer 60 during use.

Figure 6:
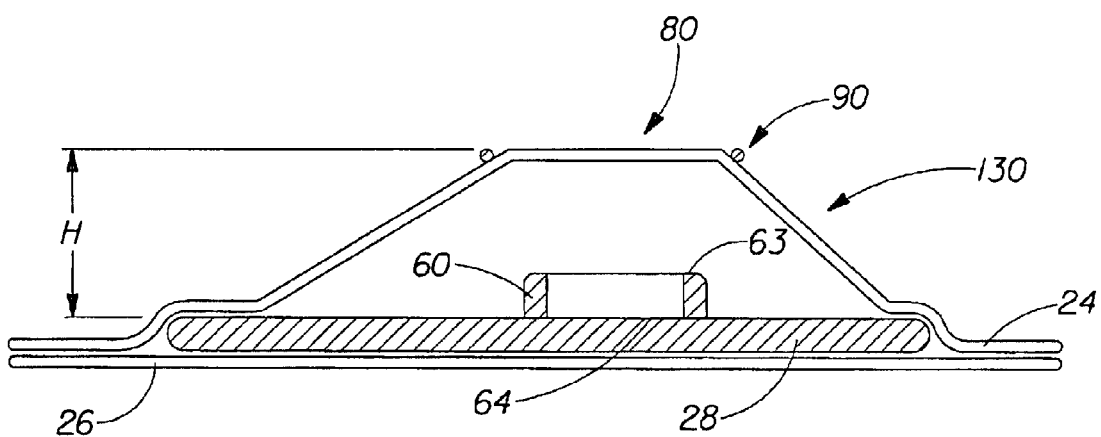
FIG. 6 is a cross-sectional view of one embodiment of the present invention.

In an alternate embodiment, as shown in FIG. 6, the topsheet 24 may be configured so at to provide a cone 130 structure when worn. As shown in FIG. 6, the cone structure is formed when the topsheet is pulled away from the core until it is restrained by an attachment to an underlying layer, such as a secondary topsheet, spacer, core, or backsheet. The cone structure 130 preferably has a height H (the height is defined as the distance above the backsheet facing side of the spacer to which the aperture 80 of the topsheet 24 may be raised under a force of less than 100 grams when the diaper 20 is in a flat configuration). The height H should not be too great or application may become difficult (i.e., the caretaker may have to take extra care or time to align the top of the cone 130 to the wearer's waste source region) or so that the cone 130 can fold over on itself during wearing and block the aperture 80. Conversely, the height H should not be too small or there may not be enough volume in the cone 130 to handle any overflow from the spacer's void space 70. A height H of between about 1.0 cm and about 10 cm is generally suitable. Preferably the height H is between about 2 cm and about 7 cm.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a first waist region, a second waist region and a crotch region located between the first waist region and the second waist region, the absorbent article further comprising:
   a topsheet including a primary aperture for receiving fecal waste,
   a backsheet joined with at least a portion of the topsheet,
   an absorbent core disposed between at least a portion of the topsheet and the backsheet,
   a spacing member disposed between the topsheet and the backsheet which provides a void space into which the fecal waste can be directed, wherein the spacing member withstands at least 0.5 psi while compressing no more than 60%, and compresses less under a pressure of about 1 psi when in a wet state than in a dry state; and
   a body adhering composition disposed about at least a portion of the primary aperture for adhering the topsheet of the absorbent article to a wearer during use.

2. The absorbent article of claim 1 wherein the primary aperture has an area between about 10 cm$^2$ and about 50 cm$^2$.

3. The absorbent article of claim 2 wherein the primary aperture has an area between about 15 cm$^2$ and about 35 cm$^2$.

4. The absorbent article of claim 1 wherein the body adhering composition includes a material selected from the following group: medical adhesives, hydrogel adhesives, gelatin, petrolatum, waxes, oils, skin care compositions.

5. The absorbent article of claim 1 wherein the body adhering composition is disposed continuously about the entire primary aperture.

6. The absorbent article of claim 1 wherein the spacing member is resilient.

7. The absorbent article of claim 1 wherein the spacing member has a void space volume of between about 10 and about 150 cm$^3$.

8. The absorbent article of claim 7 wherein the spacing member has a void space volume of between about 25 and about 75 cm$^3$.

9. The absorbent article of claim 1 wherein the spacing member has thickness of between about 0.5 cm and about 3 cm in use.

10. The absorbent article of claim 1 wherein the spacing member is joined with one or more of the following: the topsheet, the backsheet, the core or a sublayer.

11. The absorbent article of claim 1 wherein the spacing member has a compression under about 1 psi of less than about 60 percent when measured in a dry state.

12. The absorbent article of claim 1 wherein the spacing member has a compression under about 1 psi of less than about 30 percent when measured in a dry state.

13. The absorbent article of claim 1 wherein the spacing member has a compression under about 1 psi of less than about 60 percent when measured in a wet state.

14. The absorbent article of claim 13 wherein the spacing member has a compression under about 1 psi of less than about 30 percent when measured in a wet state.

* * * * *

UNITED STATES PATENT AND TRADEMARK OFFICE
CERTIFICATE OF CORRECTION

PATENT NO.   : 6,716,204 B1
DATED        : April 6, 2004
INVENTOR(S)  : Vincenzo D'Acchioli et al.

It is certified that error appears in the above-identified patent and that said Letters Patent is hereby corrected as shown below:

Column 2,
Line 3, delete "diaper." and insert -- diaper according to the present invention. --.

Column 6,
Line 48, delete "Multiple/Layer" and insert -- Multiple Layer --.

Column 13,
Line 31, delete "Nos" and insert -- Nos. --.
Line 43, delete "Type B)" and insert -- (Type B) --.
Line 44, delete "ADESIVE" and insert -- ADHESIVE --.

Column 14,
Line 34, delete "$G'_{37}/G''_{37}$" and insert -- $G'_{37}/G''_{37}$, --.

Signed and Sealed this

Twenty-eighth Day of February, 2006

JON W. DUDAS
*Director of the United States Patent and Trademark Office*

UNITED STATES PATENT AND TRADEMARK OFFICE
CERTIFICATE OF CORRECTION

PATENT NO. : 6,716,204 B1  
DATED : April 6, 2004  
INVENTOR(S) : Vincenzo D'Acchioli et al.

Page 1 of 1

It is certified that error appears in the above-identified patent and that said Letters Patent is hereby corrected as shown below:

Column 2,  
Line 3, delete "diaper." and insert -- diaper according to the present invention. --.

Column 6,  
Line 48, delete "Multiple/Layer" and insert -- Multiple Layer --.

Column 13,  
Line 31, delete "Nos" and insert -- Nos. --.  
Line 43, delete "Type B)" and insert -- (Type B) --.  
Line 44, delete "ADESIVE" and insert -- ADHESIVE --.

Column 14,  
Line 34, delete "$G'_{37}/G''_{37}$" and insert -- $G'_{37}/G''_{37}$, --.

Column 16,  
Line 18, delete "spacer 60, 61" and insert -- spacer 60 --.  
Line 32, delete "spacer 60" and insert -- spacer 60, 61 --.

Signed and Sealed this

Twenty-eighth Day of March, 2006

JON W. DUDAS  
*Director of the United States Patent and Trademark Office*